United States Patent [19]
Chang et al.

[11] Patent Number: 5,487,988
[45] Date of Patent: Jan. 30, 1996

[54] PREPARATION OF PERILLYL COMPOUNDS USING *BACILLUS STEAROTHERMOPHILUS*

[75] Inventors: Hae C. Chang, Taejeon, Rep. of Korea; Patrick J. Oriel, Midland, Mich.

[73] Assignee: Board of Trustees Operating Michigan State University, E. Lansing, Mich.

[21] Appl. No.: 290,469

[22] Filed: Aug. 15, 1994

[51] Int. Cl.$^6$ ............... C12P 7/24; C12P 7/02; C12N 1/20

[52] U.S. Cl. .......... 435/147; 435/155; 435/252.5; 435/832

[58] Field of Search ................ 435/147, 155, 435/252.5, 832

[56] References Cited

U.S. PATENT DOCUMENTS 5,110,832  5/1992  Chastain et al. .............. 514/729

OTHER PUBLICATIONS

Dhavalikar, R. S., et al., Indian J. Biochem., 3:158–164 (1966).
Erickson, R. E., Monterpenes, vol. 39, No. 1 8–19 Jan.–Feb. 1976).
Cadwallader, K. R., Journal of Food Science vol. 57, No. 1, (1992).
Kieslich et al., Transformation of terpenoids. in Progress in essential oil research. XVI. Ernst–Joachin Brunke (Eds.) 367–394 (1986).
Braddock & Cadwallader, Food Technol. 40(2): 105–110 (1992).
Krasnobajew, V., Terpenoids Ch. 4. In "Biotechnology–Biotransformations" vol. 6a. K. Lieslich (Ed.). 98–125. Verlag Chemie, Weinheim (1984).
Cadwallader et al., J. Food Sci. 54:1241–1245 (1989).
Dhavlikàr et al., Indian J. Biochem. 3:144–157 (1966).
Buchanan & Gibbons, (Eds.) Bergey's Manual of Determinative Bacteriol., 8th ed. The Williams & Wilkins Co., Baltimore, Md. 529–549 (1975).
Gurujeyalakshmi & Oriel, Appl. Environ. Microbiol. 55: 500–502 (1989).
Uribe & Pena, J. Chem. Ecol. 16: 1399–1408 (1990).
H. C. Chang and Patric Oriel, J. of Food Science 59, No. 3 660–662 (1994).

*Primary Examiner*—Marian C. Knode
*Assistant Examiner*—Francisco C. Prats
*Attorney, Agent, or Firm*—Ian C. McLeod

[57] ABSTRACT

A process for the preparation of monoterpene compounds (such as perillyl alcohol, aldehyde and α-terpineol) from limonene is described. The process uses *Bacillus stearothermophilus* which is effective at high temperatures (55° to 70° C.). A preferred strain of *Bacillus stearothermophilus* is ATCC 55596.

10 Claims, 5 Drawing Sheets

PREPARATION OF PERILLYL COMPOUNDS USING *BACILLUS STEAROTHERMOPHILUS*

BACKGROUND OF THE INVENTION (1) Field of the Invention

The present invention relates to a process for producing perillyl compounds (such as perillyl alcohol; perillyl aldehyde and α-terpineol) from limonene using *Bacillus stearothermophilus*. In particular the present invention relates to a process which produces a high production of perillyl alcohol.

(2) Description of Related Art

The monocyclic terpenoid (+) limonene ((R)1-cyclohexen-1-methyl 4-(1-methylethyl)) is an attractive monoterpene starting material for microbial bioconversion to higher value monoterpenes utilized in flavor and perfume applications (Kieslich et al., Transformation of terpenoids. in Progress in essential oil research. XVI. Ernst-Joachin Brunke (Ed.). 367–394 (1986)). (+) Limonene is a common constituent of many essential oils and is the major component in oils derived from citrus product waste peels (Braddock and Cadwallader, Food Technol. 40(2):105–110 (1992)). As a result, it is one of the least expensive and widely available terpenes, and is used directly in a number of food and other applications (Krasnobajew, V., Terpenoids Ch. 4. In "Biotechnology-Biotransformations" Vol 6a. K. Lieslich (Ed.). 98–125. Verlag Chemie, Weinheim (1984)). Useful oxidation products of (+) limonene include perillyl alcohol ((R)1-cyclohexene-1-methanol-4-(1-methylethyl)); perillyl aldehyde ((R)1-cyclohexene-1-carboxaldehyde 4-(1-methylethyl)), and perillic acid ((R)1-cyclohexene-1-carboxylic acid-4-(1-methylethyl)). These are naturally found in low quantities in citrus, lemon grass, and perilla oils, and are utilized as flavorings and as antimicrobial agents in food and pharmaceuticals.

The possibility of microbial conversion of limonene to other monoterpenes of interest has been examined, and bacteria have been isolated which are capable of growth on limonene yielding metabolites such as (+)-α-terpineol, (+)-limonene-1,2-diol, (+)-perillic acid, and (+)-β-isopopenyl pimelic acid (Cadwallader et al, J. Food Sci. 54:1241–1245 (1989); Dhavlikar et al, Indian J. Biochem. 3:144–157 (1966); and Krasnabajew, V., Terpenoids Ch. 4. In "Biotechnology-Biotransformations" Vol 6a. K. Lieslich (Ed.). 98–125. Verlag chemie, Weinheim (1984)). While these studies are of scientific interest, commercialization of these processes has been thwarted by the multiplicity of conversion products produced, and the low conversion product concentrations due to the toxicity of limonene to most microorganisms.

U.S. Pat. No. 5,110,832 to Chastain et al shows that bacteria, particularly Bacillus are killed by perillyl alcohol. Thus, there is a problem in finding bacteria which will metabolize limonene, in itself inhibiting to the bacteria, to a compound which kills the bacteria.

OBJECTS

It is therefore an object of the present invention to provide a process using bacteria which are uniquely adapted to producing the perillyl compounds in significant yield from limonene. Further, it is an object of the present invention to provide a process which is relatively simple and economical. These and other objects will become increasingly apparent by reference to the following description and the drawings.

BRIEF DESCRIPTION OF DRAWINGS

FIG. 4A shows the bacterial control extract without limonene.

FIG. 4B shows the limonene control extract. In the chromatogram: 1 is limonene; 2 is 1,8-cineole; 3 is bicyclic monoterpene; 4 is α-terpineol; 5 is isomer-perillyl aldehyde; and 6 is perillyl alcohol.

DESCRIPTION OF PREFERRED EMBODIMENTS

Figure 1:
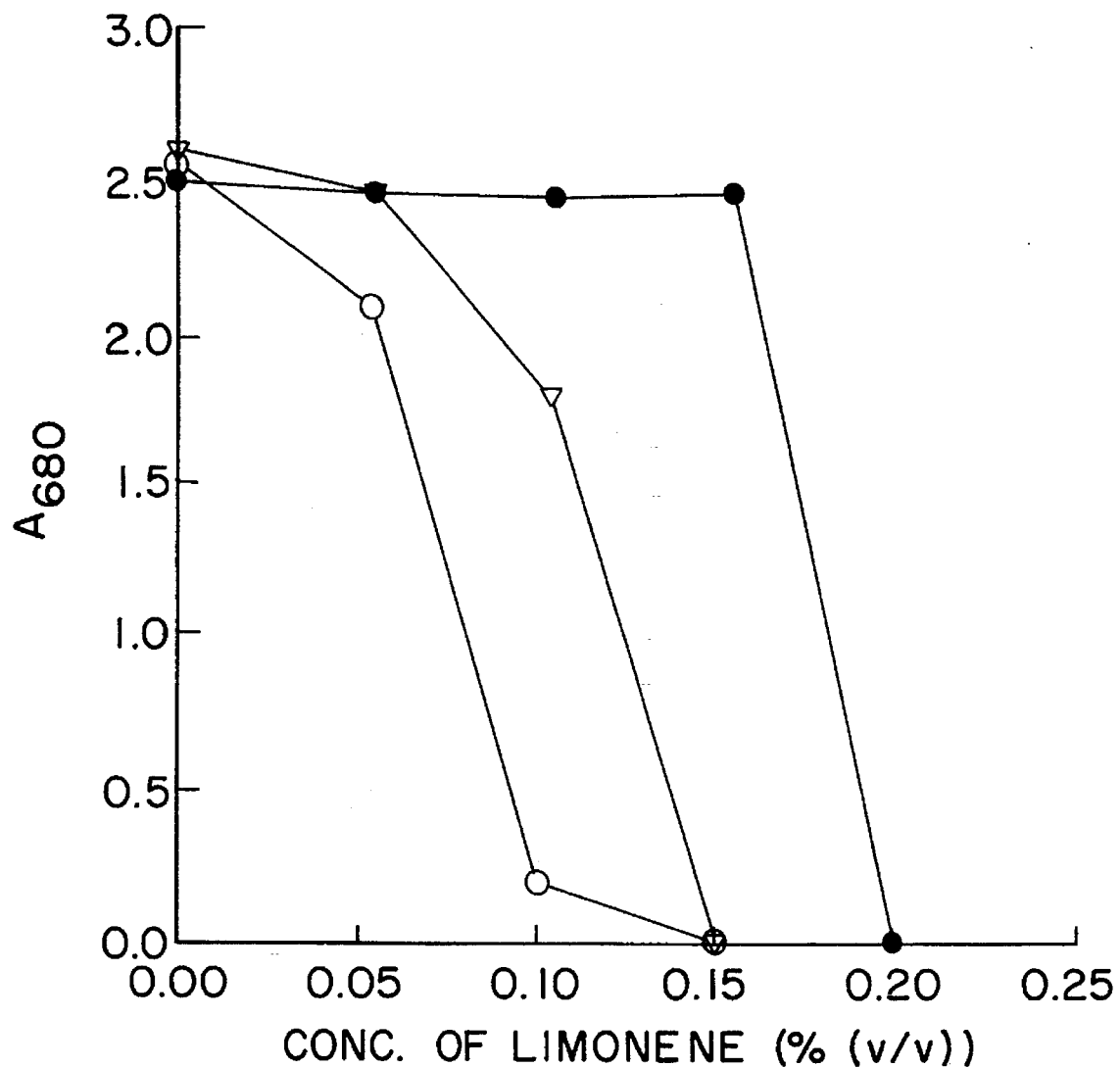
FIG. 1 is a graph showing growth inhibition by (+)limonene of *Bacillus stearothermophilus* strains BR388, BR389, and BR316. The symbols are: o, BR316; Δ, BR389; •, BR388.

The present invention relates to a process for producing monoterpene compounds which comprises providing a culture medium containing cells of *Bacillus stearothermophilus*; and incubating the cells in the culture medium in the presence of limonene to produce isolatable amounts of the monoterpene compounds. The incubating is preferably at a temperature between about 55° and 70° C.

The present invention also relates to *Bacillus stearothermophilus* as an isolated pure culture of citrus skin which degrades limonene to a perillyl compound.

The limonene is preferably provided in the culture medium as a vapor so that the cells are not inhibited. The limonene can also be added in small increments over time directly to the culture medium. All of these means of providing the limonene in the culture medium are well known to those skilled in the art.

Preferably the culture medium contains yeast extract or another protein and amino acid source which is assimilable by the *Bacillus stearothermophilus*. The remainder of the culture medium is one which is standard for growing Bacillus and is available from numerous sources, such as Difco, Detroit, Mich.

The monoterpene compounds formed are separated from the culture medium. This is easily accomplished by organic solvent extraction, preferably using diethyl ether. the individual compounds can be separated using liquid chromatography or other means known to the art.

The preferred source of the *Bacillus stearothermophilus* is citrus skin, particularly orange peel or skin. The most preferred strain is *Bacillus stearothermophilus* ATCC 55596 (BR 388) which has been deposited under the Budapest Treaty with the American Type Culture Collection in Beltsville, Md.

EXAMPLE 1

Bacillus stearothermophilus ATCC 55596 (BR388) was isolated from orange peel by an enrichment culture using (+)-limonene. The thermophilic isolate exhibited growth between 45° and 68° C., with an optimum growth temperature near 55° C. BR388 could grow on limonene as a sole carbon source, but grew and degraded limonene more effectively when supplemented with low amounts of yeast extract. Perillyl alcohol was identified as the major conversion product, with α-terpineol and perillyl aldehyde formed as minor products. Strains of *Bacillus stearothermophilus* previously isolated from aromatic enrichments were also shown able to grow on limonene, but demonstrated higher toxicity by limonene than BR388.

MATERIALS & METHODS

Reagents (+)limonene and (+)perillic acid was obtained from Aldrich Co. Milwaukee, Wis. (+)Perillyl alcohol and (+)perillyl aldehyde was purchased from Nippon Terpene Chemical Co., Kobe, Japan.

Microorganism Isolation

Thermophiles capable of growth on limonene were isolated by inoculation of small pieces of orange peel into a 50 ml of DP salt media (per liter: $NH_4Cl$, 1.0 g; $K_2HPO_4$, 0.5 g; $MgSO_4.7H_2O$, 20 mg; pH 7.2) with 1 ml of neat (+)limonene (97% purity) in a 125 ml of screw-cap bottle, and incubation at 55° C. with shaking. After 24 hours incubation, 100–200 μl of the culture were plated onto DP salt agar media in Petri dishes containing 100 μl of limonene in a small glass tube attached to the cover, and incubated at 55° C. Cultures demonstrating growth on repeated transfer were retained as putative limonene users.

Toxicity test of limonene.

To determine the relative toxicity of limonene, thermophile isolates were cultured in LB broth (Bacto-tryptone, 10 g; yeast extract, 5 g; NaCl 5 g per liter) containing concentrations of (+)limonene between 0–0.2% (v/v). Growth was observed using turbidity.

Growth and Biotransformation.

Triple-baffled 250 ml nephelo culture flasks with cleanout arm and depressed side arm (Bellco Inc. Vineland, N.J.) were used for thermophile growth and biotransformation studies. This flask allowed vapor introduction of (+)limonene into the culture from liquid contained in the side arm. The medium for growth and limonene transformation contained 75 ml of DP salt and vitamin complex (0.4 mg nicotinamide, 0.4 mg of thiamine and 2 μg biotin per liter) either alone or supplemented with 0.0125% yeast extract. Cultures were incubated at 55° C. in a gyratory shaking water bath. Relative growth at various temperatures was measured by measurement of culture turbidity with time using samples measured at 550 nm in a Gilford (Model 240) single beam spectrophotometer corrected for absorbance of the medium. Maximum specific growth rates at various temperatures were obtained using the maximum slope of semi-log plots of turbidity with time.

Extraction of the biotransformation products.

To recover biotransformation products, 16–36 hour cultures were centrifuged at 12,800×g for 20 minutes at 4° C. Following passage through a Millipore (Bedford, Mass.) 0.45 μm filter, the filtrate was acidified to pH 2.0 and extracted (3×0.5 vol.) with ether. The ether fraction was evaporated to 25 ml and separated into neutral and acidic fractions by extraction (3×0.6 vol.) with 5% (w/v) NaOH solution. The ether fraction was concentrated under a stream of nitrogen, neutralized with 5% (v/v) HCl and then analyzed by high performance liquid chromatography (HPLC) and gas chromatograph-mass spectrograph (GC-MS) using procedures of Cadwallader et al., J. Food Sci. 54:1241–1245 (1989). The NaOH fraction was acidified to pH 2.0 and re-extracted (3×0.3 vol.) with ether. The ether fraction was concentrated under a stream of nitrogen and then analyzed by HPLC and GC-MS.

Analytical methods.

Products were analyzed by HPLC for routine analysis and analyzed by GC-MS for product identification. The HPLC system used was a HP 1050 series (Hewlett Packard, Bedford, Mass.). Injection volume was 5.5 μl, volumes for draw speed and eject speed were each 200 μl/ml. Separation utilized a 3.9 mm×15 cm NOVA-PAK C18 column (Millipore Co.) equipped with 3.2×15 mm RP-18 Brownlee New 7 micron guard column (Anspec Co.). Peaks were detected at 245 nm using a HP1050 series multiple wavelength detector. Samples were eluted using a 20 min linear gradient from 99.9% water to 99.9% acetonitrile with an initial hold time of 1 min and a second hold time of 5 min and again a 8 min linear gradient from 99.9% acetonitrile to 99.9% water.

The GC-MS system utilized was a mass spectrometer HP 5970 coupled with gas chromatograph HP 5890 (Hewlett Packard, Campus, Wash.). The mass selective detector was a MSD HP 5970 (Hewlett Packard). A 0.25 mm I.D.×30 m DB-wax fused silica capillary column was used for separation. Conditions were as follows: 1 μl injection; helium carrier gas; injection port and detector port at 240° C.; column temperature programmed from 40°–240° C. at 7° C./min. with a 2 min. initial hold time.

Microorganism Isolation and characterization.

Two colonies, designated BR388 and 389 were isolated from limonene enrichment culture using an orange peel inoculum. Both demonstrated growth at 55° C. on DP plates utilizing limonene as the sole carbon source, producing small creamy colonies in 3 to 4 days. Both isolates were rods of approximately 3 to 4 μm length, demonstrated variable Gram staining, and produced oval spores under starvation conditions. These characteristics, and their ability to grow well under aerobic conditions at 65° C. are consistent with those of the broadly-defined species *Bacillus stearothermophilus* (Buchanan and Gibbons, (Ed.) Bergey's Manual of Determinative Bacteriology, 8th ed. The Williams & Wilkins Co., Baltimore, Md. 529 to 549 (1975)), to which we have tentatively assigned them. They are differentiated from *Bacillus schegellii*, which can also grow aerobically at 65° C. by shorter cell length, lower optimum growth temperature, and oval rather than spherical spore shape. Two other *Bacillus stearothermophilus* strains BR316 and BR219 (Gurujeyalakshmi and Oriel, Appl. Environ. Microbiol. 55:500–502 (1989)), which isolated from toluene and phenol enrichments, respectively, were also tested for growth on limonene. Of these, BR316 demonstrated this ability, and was retained for further testing.

Limonene tolerance

Limonene is toxic to many microorganisms, even at low concentrations (see, for example Uribe and Pena, J. Chem. Ecol. 16;1399–1408 (1990)). To test the ability of thermophile isolates BR388, BR389 and BR316 to withstand limonene toxicity, we observed their growth in rich medium containing limonene at concentrations between (0.0–0.25% (v/v)). Results in FIG. 1 show relative growth rates of the isolates. It should be noted that the concentration of limonene shown is that added, uncorrected for volatilization. In these studies, BR388 demonstrated higher resistance to limonene toxicity than BR389, which in turn was more resistant than BR316 which was not isolated from a limonene-containing environment. As a result of these tests, BR388 was selected for biotransformation studies.

Determination of optimum growth temperature

Figure 2:
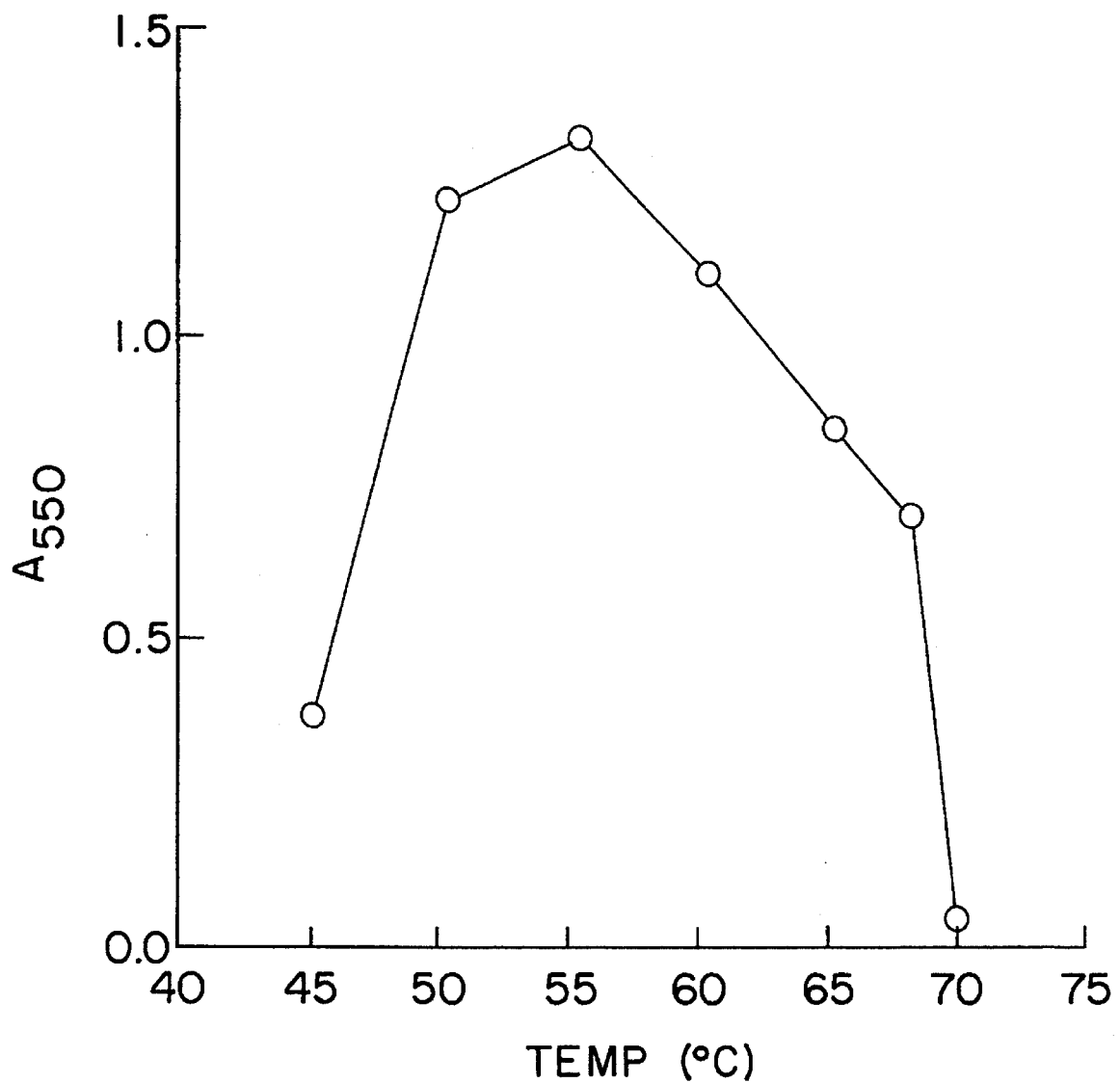
FIG. 2 is a graph showing an optimum growth temperature of Bacillus stearothermophilus BR388.

To verify that *Bacillus stearothermophilus* BR388 was an obligate thermophile, growth in LB medium temperatures from 45° C. to 70° C. was measured. As seen in FIG. 2, BR388 grew well between temperatures of 45° and 68° C. The optimum growth temperature was a 55° C. with a maximum specific growth rate of 2.4 hr$^{-1}$ was observed.

Growth of BR388 in liquid culture

Figure 3:
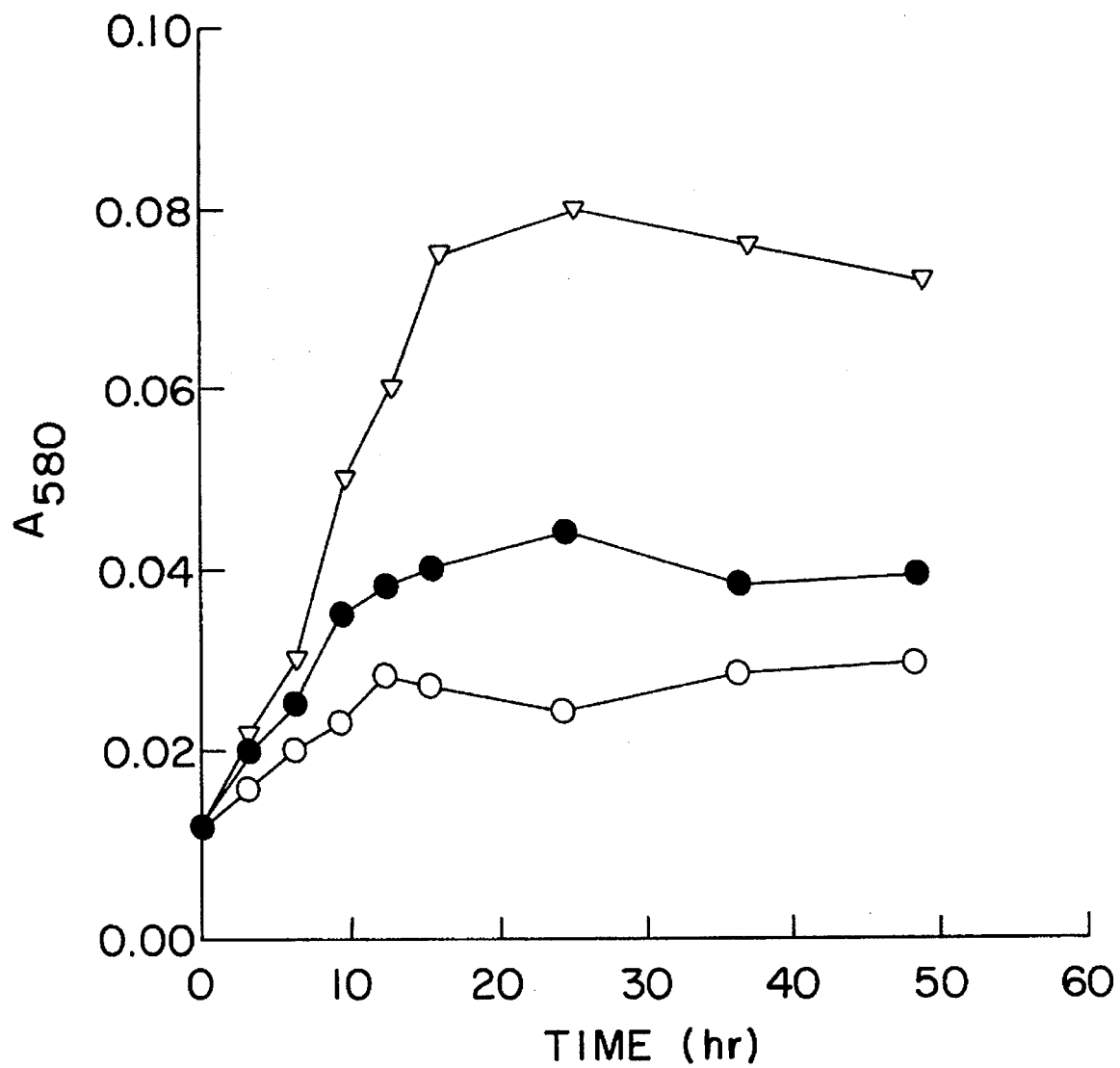
FIG. 3 is a graph showing growth of *Bacillus stearothermophilus* BR388 in DP minimal broth. The symbols are: Δ: with limonene and with yeast extract; ●: without limonene and with yeast extract; ○: with limonene and without yeast extract.

Growth of *Bacillus stearothermophilus* BR388 in DP minimal medium with limonene is shown in FIG. 3. Although the isolate was able to grow in this medium, biomass levels were modest. To enhance growth, 0.125 gm/l yeast extract was added for supplementation. As seen in FIG. 3, this level of yeast extract supported a low level of growth in the absence of limonene, but with significantly enhanced biomass in the presence of limonene.

EXAMPLE 2

Examination of limonene bioconversion products

Figure 4A:
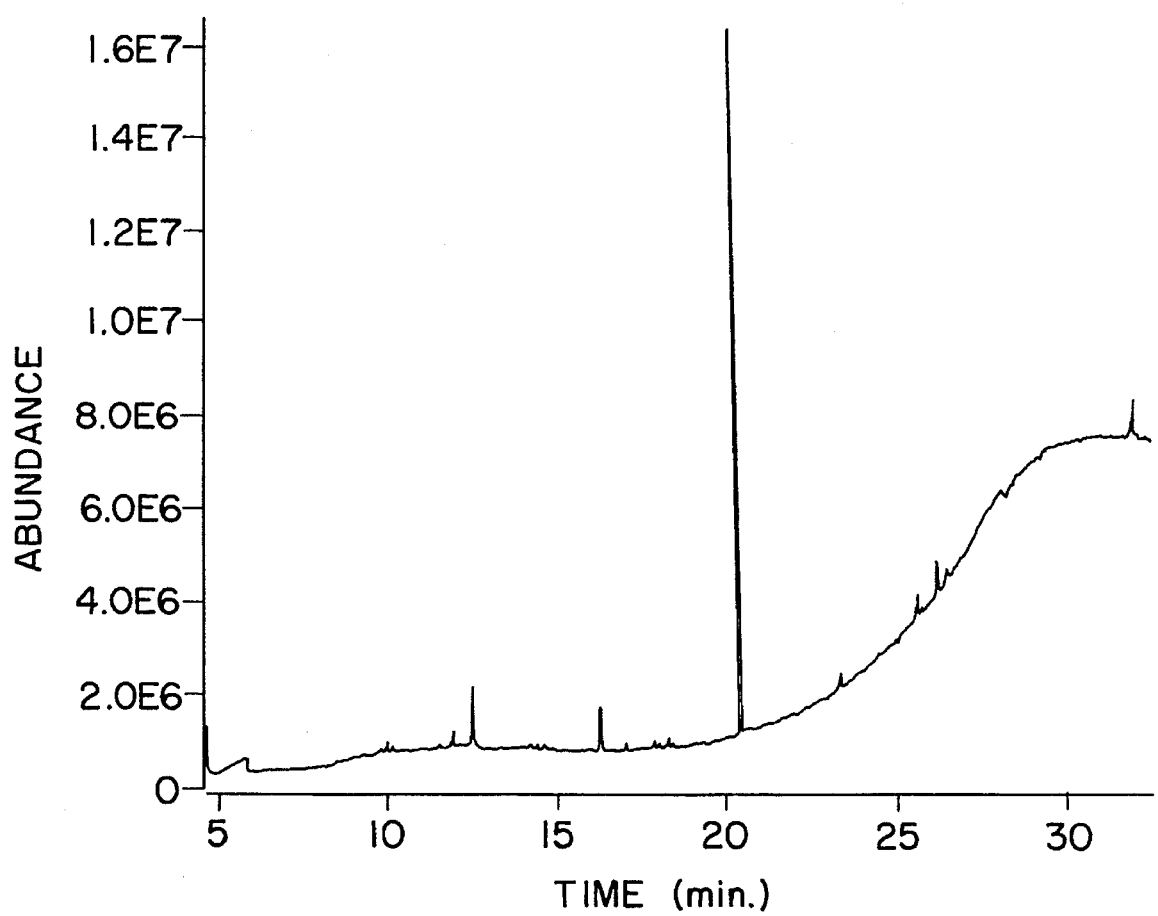
FIGS. 4A and 4B show gas chromatograms (GC) of bioconverted compounds from limonene by *Bacillus stearothermophilus* BR388.
Figure 4B:
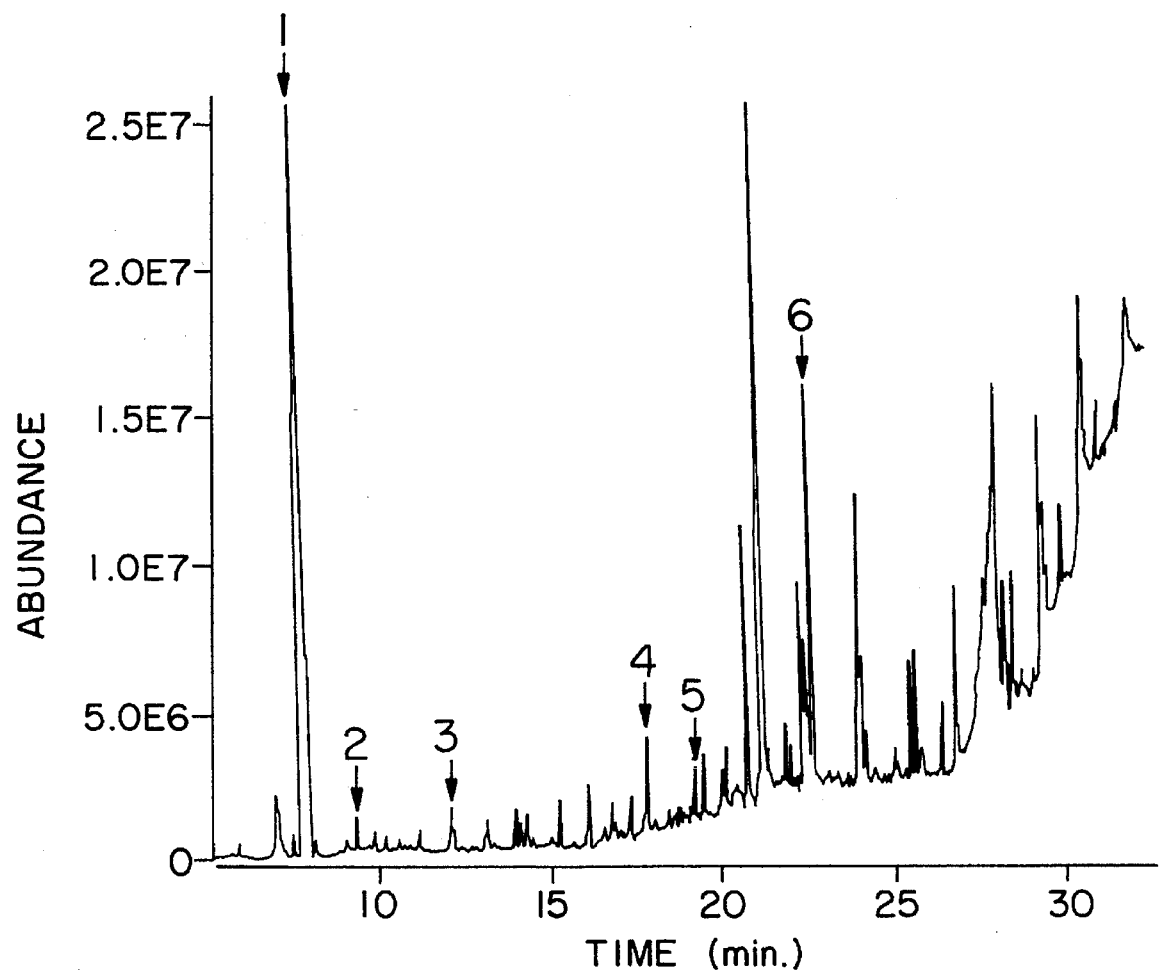

Growth of *Bacillus stearothermophilus* BR388 on DP minimal medium as in Example 1 supplemented with 0.0125% yeast extract and limonene vapor resulted in formation of multiple metabolites, the number and amounts of which varied with culture time. From the GC-MS chromatograms of the neutral fraction (FIG. 4B), perillyl alcohol was identified as a major component, reaching levels of 200 µg/ml of culture. Control cultures with no limonene vapor (FIG. 4A) did not produce this metabolite. Other metabolites present in lower amounts included were α-terpineol, perillyl aldehyde, bicyclo(2,2,1)-hepten-2-one, cyclohexanol and 1,8-cineole. Highest yield of perillyl alcohol were obtained from cultures in the exponential phase (data not shown). α-terpineol, perillyl alcohol and perillyl aldehyde are monoterpenes (as is limonene). Perillic acid was not observed.

The broad metabolic capability of *Bacillus stearothermophilus* includes utilization of limonene which results in monoterpenes of interest.

Certain aspects of the present invention are described by the inventors in J. of Food Science 59 660–662 (June 1994) which is incorporated herein by reference. It is intended that the foregoing description be only illustrative of the present invention and that the present invention be limited only by the hereinafter appended claims.

We claim:

1. A process for producing perillyl compounds which comprises:

(a) providing a culture medium containing cells of a strain of *Bacillus stearothermophilus* having all the identifying characteristics of *Bacillus stearothermophilus* ATCC 55596;

(b) incubating the cells in the culture medium with limonene to produce isolatable amounts of the perillyl compounds in the culture medium; and (c) recovering the perillyl compounds from the culture medium.

2. The process of claim 1 wherein the culture medium contains yeast extract.

3. The process of claim 1 wherein the limonene is introduced into the culture medium as a vapor.

4. The process of claim 1 wherein the recovering is by extraction with an organic solvent.

5. The process of claim 4 wherein the solvent is ether.

6. The process of claim 1 wherein the incubating is at a temperature between about 55° and 70° C.

7. The process of claim 1 wherein the culture medium contains yeast extract, is incubated at a temperature between about 55° and 70° C., and the limonene is a vapor.

8. The process of claim 7 wherein the perillyl compounds are recovered from the culture medium by extraction with diethyl ether.

9. The process of claim 1 wherein the perillyl compounds comprise perillyl alcohol, perillyl aldehyde and α-terpineol.

10. The process of claim 1 wherein the *Bacillus stearothermophilus* is ATCC 55596.

\* \* \* \* \*